(12) United States Patent
Livingston

(10) Patent No.: US 11,426,252 B2
(45) Date of Patent: Aug. 30, 2022

(54) APPARATUS AND METHOD FOR FIXATION OF TISSUE IN SECONDARY AND TERTIARY PLANES DURING MEDICAL IMAGING, EXAMINATION, AND INTERVENTION

(71) Applicant: Lisa Livingston, San Antonio, TX (US)

(72) Inventor: Lisa Livingston, San Antonio, TX (US)

( * ) Notice: Subject to any disclaimer, the term of this patent is extended or adjusted under 35 U.S.C. 154(b) by 929 days.

(21) Appl. No.: 16/221,085

(22) Filed: Dec. 14, 2018

(65) Prior Publication Data

US 2020/0188056 A1    Jun. 18, 2020

(51) Int. Cl.
| | | |
|---|---|---|
| *A61B 90/17* | (2016.01) |
| *A61B 5/00* | (2006.01) |
| *A61B 8/08* | (2006.01) |
| *A61B 6/00* | (2006.01) |
| *A61B 5/055* | (2006.01) |

(52) U.S. Cl.
CPC .............. *A61B 90/17* (2016.02); *A61B 5/055* (2013.01); *A61B 5/708* (2013.01); *A61B 6/502* (2013.01); *A61B 5/4312* (2013.01); *A61B 8/0825* (2013.01)

(58) Field of Classification Search
CPC ....... A61B 90/17; A61B 5/4312; A61B 5/708; A61B 6/502; A61B 6/0421; A61B 8/0825; A61B 8/40
See application file for complete search history.

*Primary Examiner* — Jason M Ip
(74) *Attorney, Agent, or Firm* — Kammer Browning PLLC

(57) ABSTRACT

A device for fixing the outer boundaries of a region of body tissue in a secondary plane (and optionally in a tertiary plane) during medical imaging, examination, and/or intervention. The caliper device includes a caliper bar with two sliding caliper arms that provide fixation of the region of tissue in the secondary plane. One embodiment provides tertiary fixation with a center plate fixator that extends from a center plate positioner. The caliper device is positioned around the region of body tissue within the primary plane fixation instrumentation. The caliper arms (and optionally, the center plate fixator) move together to "thicken" the region of tissue between them. The device is preferably constructed of radiotransparent material and for single-use applications.

20 Claims, 6 Drawing Sheets

APPARATUS AND METHOD FOR FIXATION OF TISSUE IN SECONDARY AND TERTIARY PLANES DURING MEDICAL IMAGING, EXAMINATION, AND INTERVENTION

BACKGROUND OF THE INVENTION

1. Field of the Invention

The present invention relates generally to devices and methods for in situ imaging, examination, and intervention of extended regions of body tissue. The present invention relates more specifically to devices and methods that facilitate the fixation of a region of body tissue in secondary and tertiary planes in addition to established practices fixing the extended region of tissue in a primary plane.

2. Description of the Related Art

There are many instances where the medical imaging of body tissue, the examination of body tissue, or the medical intervention into a region of body tissue, require a stable fixation of the tissue for accuracy in carrying out the procedure. A typical example of such a procedure involves imaging and intervention into breast tissue for purposes of identifying and addressing anomalous cell structures or mineral accumulations. Most current mammography practices, as examples, involve efforts to fix the breast tissue in a primary plane, across which x-ray imaging may be used to help identify targets of anomalous growth or accretions. One of the problems associated with accurately imaging regions of tissue that extend from the body, is maintaining the tissue in a fixed, referenced, spatial framework long enough to carry out the imaging procedure. In addition to the typically pliable nature of the tissue, the inevitable motion of the alert individual (patient) during the procedure complicates the maintenance of accuracy, especially when only one plane of fixation is established.

Post diagnostic imaging procedures, such as tagging, biopsy, and excision, also rely on an accurate fixation of the tissue for successful procedures. There are many procedures and techniques for post imaging intervention that are computer assisted operations based upon the previous placement of tags or markers on the anomalous feature. In most cases, accuracy in carrying out these procedures is facilitated by having an optimal thickness of tissue within the space under examination to access or target an anomaly and to place its position in a sufficiently accurate dimension in the plane of examination. Where the volume of the extended region of tissue is small, fixing the tissue in a primary plane often serves to reduce the thickness of the tissue to a point where accessing a very small target within the tissue becomes quite difficult. Efforts to reduce the compression of the region of tissue in the primary plane to improve "thickening" often result in insufficient fixation of the tissue for accuracy.

Some efforts have been made to "fix" a region of tissue within three dimensions to provide improved resolution and accuracy. Some existing systems simply orient the region of tissue such that gravity serves to extend and somewhat stabilize the region for examination. Some existing systems use negative pressure to draw the region of tissue into a confined space. Each of these systems requires its own unique instrumentation and are not adaptable for use with any other existing systems. In addition, none of these existing systems provide a sufficiently firm fixation of the region of tissue that is typically required to maintain location accuracy on a target through imaging, examination, and intervention procedures.

It would be desirable to have a means for fixing in space a region of body tissue for purposes of improving accuracy in imaging, examination, diagnostics, and intervention. It would be particularly helpful to have a device that could stabilize (fix) and then "thicken" smaller regions of tissue that would otherwise not provide sufficient volume with the use of a system that only functions in a single (primary) plane. It would further be desirable if such a fixation device could be used in association with a wide range of existing systems that serve to fix the region of tissue in only a single plane, without requiring significant or permanent alteration of the structures of the existing system. It would further be desirable if such a fixation device could be used in conjunction with a wide range of different imaging modalities including x-ray, magnetic resonance, visual light, infrared light, ultrasound, etc. It would be beneficial if such a device were easy to position and adjust so as to minimize the time during which the patient is subjected to the tissue fixation procedure. Finally, it would be beneficial if such a device were inexpensive to manufacture such that single-use products could be produced.

SUMMARY OF THE INVENTION

The present invention therefore provides a device for fixing the outer boundaries of a region of body tissue in a secondary plane (and optionally in a tertiary plane) during medical imaging, examination, and/or intervention, where the region of body tissue is being fixed in a primary plane by existing instrumentation. The caliper device is made up of a caliper bar with two parallel sliding caliper arms that provide fixation of the region of tissue in the secondary plane. Each of the caliper arms preferably includes a mechanism for fixing the caliper arm in a stable position on the caliper bar and alternately releasing the caliper arm to again slide along the caliper bar.

In an alternate embodiment that additionally provides tertiary fixation, the caliper device of the present invention includes a center fixation assembly with a center plate fixator mounted on a center plate bar (oriented orthogonally to the caliper bar) that extends slidingly through a center plate positioner. The center plate positioner may be either fixed to a center point on the caliper bar or may slide along the caliper bar in a manner similar to the caliper arms. The center plate positioner preferably includes a mechanism for fixing the center plate bar (and therefore the center plate fixator) in a stable position within the center plate positioner and alternately releasing the center plate bar to again slide through the center plate positioner.

In use, the caliper device is positioned with the open caliper arms on opposing sides of the region of body tissue, between the typical movable parallel plates of the primary plane fixation instrumentation. The caliper arms are moved towards each other to "thicken" the region of tissue between them. If used, the center plate fixator is directed towards the region of tissue to further limit the outer boundary of the region of tissue in the tertiary plane. The parallel planar members (plates) of the primary plane fixation system are then moved towards each other to set the outer boundaries of the region of tissue in the primary plane. Although the device would most frequently find use with existing instrumentation that provides two horizontal planar members for fixing the tissue in the primary plane, it is capable of being used with the primary plane of fixation being in anything from a horizontal to a vertical orientation.

The device of the present invention optimizes the spatial dimensions of a region of body tissue for purposes of imaging, examination, diagnostics, and intervention. The device can improve repeatability of measurements and location such that accuracy can be maintained at each stage of the process of identifying and treating undesirable anomalies within the tissue. Although the device is sufficiently variable to accommodate a wide range of body tissue shapes and sizes, small, medium, and large caliper devices may be structured to increase the range of use. The device is preferably constructed of radiotransparent material and finds some advantage in being constructed of visual light transparent material (such as clear Lucite or other clear polymer plastics). Although the device may be constructed for multiple uses, the components are sufficiently inexpensive to manufacture as to make single-use production of the device practical. Multiuse versions of the device may include disposable covers for the caliper arms and center plate fixator.

DETAILED DESCRIPTION OF THE PREFERRED EMBODIMENTS

Figure 1:
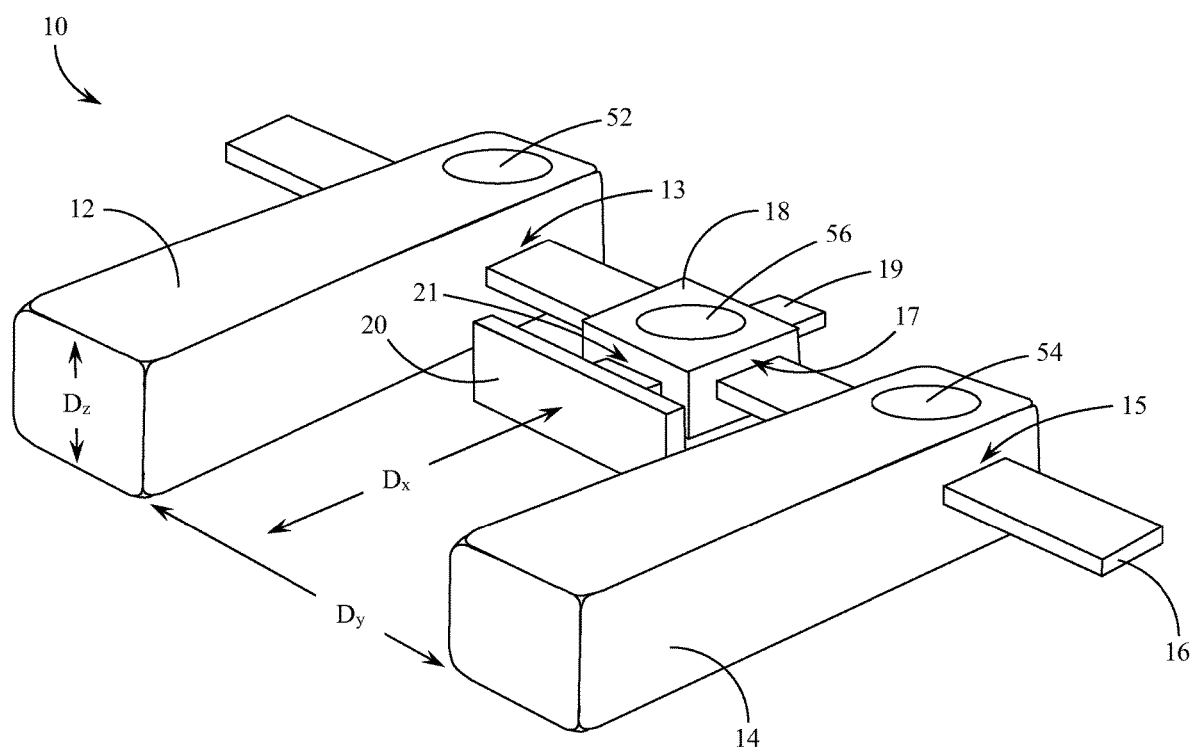
FIG. 1 is a perspective view of the device of the present invention shown in an open condition ready for application and use.

Use of the terms "distal" and "proximal" herein will generally refer to directions away from ("distal") and towards or close to ("proximal") the patient or individual whose region of body tissue is being examined. Reference is made first to FIG. 1 for a perspective view of a first preferred embodiment of the device of the present invention shown in an open condition ready for application and use. Tissue fixation caliper 10 generally comprises first caliper arm (secondary plane fixation) 12 and second caliper arm (secondary plane fixation) 14 which engage with and slide along caliper bar 16. Caliper bar 16 extends through ratcheting aperture 13 in first caliper arm 12 and through ratcheting aperture 15 in second caliper arm 14. The ratcheting mechanisms associated with each caliper arm 12 & 14 are preferably structured to allow free sliding movement of the arms inward towards a center point on caliper bar 16, but to resist outward movement on the bar unless sliding ratchet release mechanism 52 (for caliper arm 12) or sliding ratchet release mechanism 54 (for caliper arm 14) are activated. An example of the manner in which sliding ratchet release mechanisms 52 & 54 may be structured is described in more detail below with reference to FIG. 3A. In general, however, caliper arms 12 & 14 may freely slide towards each other on caliper bar 16 and experience some resistance to the opposite motion (outward) until the appropriate release mechanisms 52 & 54 are activated.

Figure 2:
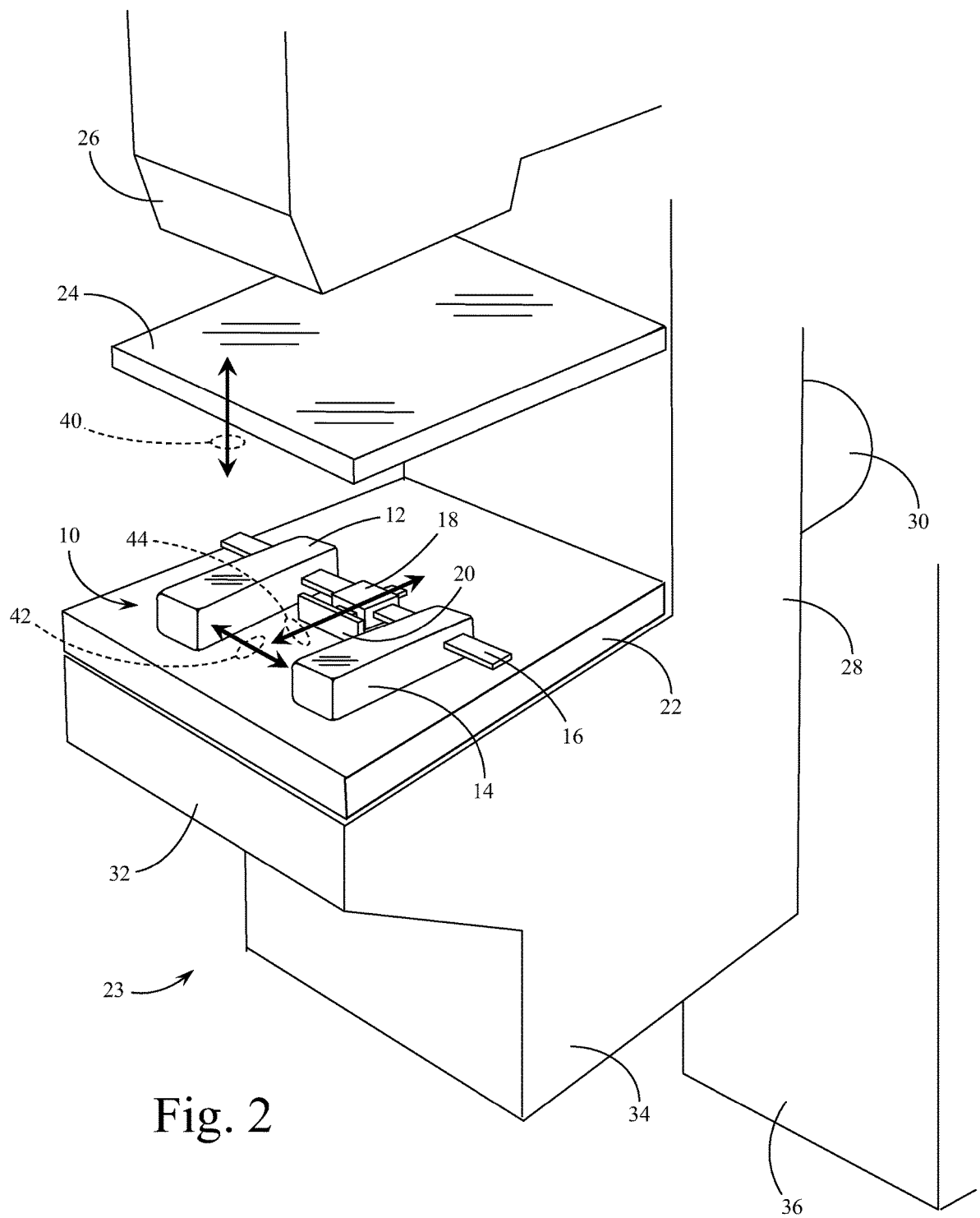
FIG. 2 is a perspective view of the device of the present invention shown positioned for use on a medical imaging system in the nature of mammography instrumentation.

The above described components of tissue fixation caliper 10 are directed to the fixation of a region of tissue in a secondary plane while the same region of tissue is being fixed in a primary plane according to traditional means (see FIG. 2). Included in the first preferred structure of tissue fixation caliper 10 is a tertiary plane fixation mechanism comprising center plate fixator 20. The assembly that positions center plate fixator 20 includes center plate positioner 18 and center plate bar 19. Center plate fixator 20 is positioned on one end of center plate bar 19 which extends slidingly through ratcheting aperture 21 in center plate positioner 18. In a manner similar to caliper arms 12 & 14 on caliper bar 16, center plate positioner 18 engages center plate bar 19 to allow free movement of center plate fixator 20 away from center plate positioner 18 and to resist movement in an opposing direction. Activation of a sliding ratchet release mechanism 58 (see FIG. 3A) allows center plate fixator 20 to slidingly return towards center plate positioner 18.

Center plate positioner 18 may be fixed in a central position on caliper bar 16 or may alternately slide along caliper bar 16 through aperture 17 to laterally reposition center plate fixator 20 between caliper arms 12 & 14. Aperture 17 must be offset from ratcheting aperture 21 if center plate positioner 18 is structured to slide along caliper bar 16. If not fixed on caliper bar 16, center plate positioner 18 may include an additional ratcheting mechanism, with sliding ratchet release mechanism 56, to engage caliper bar 16 in the same manner as caliper arms 12 & 14. Although during use there is generally no lateral force exerted on center plate positioner 18 it is still preferable that there be a means to fix it in position on caliper bar 16.

As shown in FIG. 1, tissue fixation caliper 10 adjusts to alter (and thereby fix) secondary and tertiary planes in the spatial volume occupied by the region of tissue. The primary plane is fixed by traditional means (again, see FIG. 2 for example) and may be limited by the thickness $D_z$ of each caliper arm 12 & 14. The secondary plane is fixed by the caliper arms 12 & 14 and varies spatial width $D_y$. The tertiary plane is fixed by center plate fixator 20 on one side and the body of the individual (patient) on the other, and correspondingly varies spatial depth $D_x$.

Reference is next made to FIG. 2 for a perspective view of the device of the present invention shown positioned for use on a medical imaging system (mammography instrumentation, as an example). In the view of FIG. 2, tissue fixation caliper 10, is again seen to be made up of caliper arms 12 & 14, caliper bar 16, center plate positioner 18, and center plate fixator 20. Tissue fixation caliper 10 is positioned on a typical primary plane fixation system 23 with two generally parallel planar functional members including image detection plate 22 and compression plate 24. Both parallel planar members may be moveable towards each other or one may be fixed (plate 22 in the example of FIG. 2) and the other moveable (compression plate 24 in the example of FIG. 2). Upper imaging arm section 26 typically houses the imaging radiation source while lower imaging arm section 34, which includes detector support platform 32, typically houses the detector array for the imaging system.

In addition to moving closer together, the parallel planar members are typically structured on a rotating imaging assembly 28 with upper imaging arm section 26 and lower imaging arm section 34. This imaging assembly 28 typically serves to raise and lower arm sections 26 & 34 by way of structures on imaging system base 36, as well as rotate the associated parallel planar members by way of imaging assembly rotation support 30. In the example shown in FIG. 2, the existing orientation of the parallel planar members (image detection plate 22 and compression plate 24) provides a horizontal surface on which tissue fixation caliper 10 may be positioned. While this may be a preferred orientation for use of the present invention, other orientations, including a vertical orientation, can be accommodated with appropriate handling of the device by the radiology technician. The manner in which the device of the present invention is positioned on the primary plane fixation system and around the region of tissue of concern is described in more detail below.

The three motion arrows shown in FIG. 2 identify the three planes of fixation achieved by the combination of the device of the present invention and the existing primary plane fixation system. The primary plane of fixation 40 is generally established by the existing system while the secondary plane of fixation 42 and the tertiary plane of fixation 44 are established by the device of the present invention. It should again be noted that although FIG. 2 discloses a typical imaging system that finds application of the present invention, the tissue fixation caliper 10 finds use with other manners of tissue examination and in particular with intervention procedures that may or may not rely upon contemporaneous imaging. The present invention will improve the results of most any procedure that currently relies solely on tissue fixation in only a single plane.

Figure 3A:
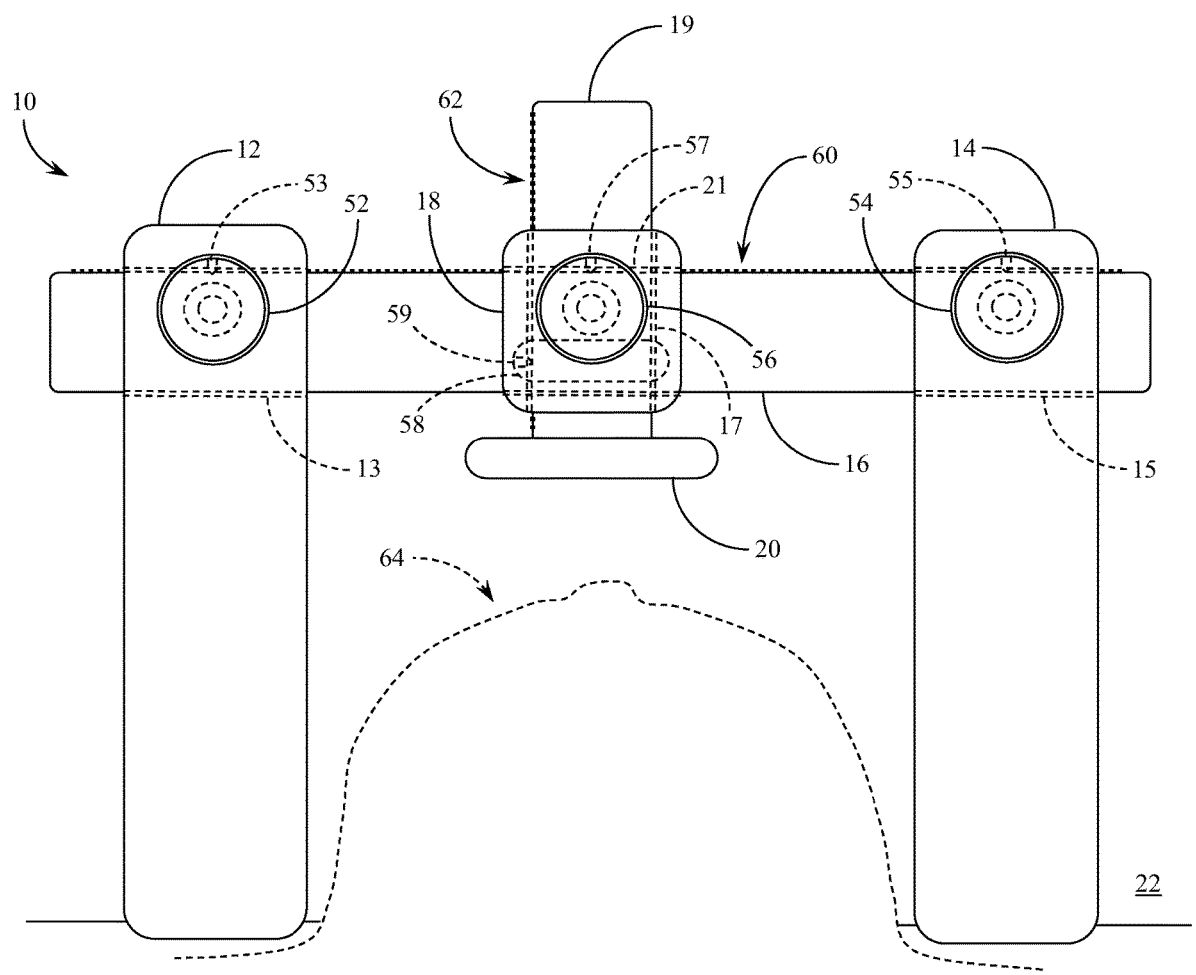
FIG. 3A is a top plan view of the device of the present invention in use in connection with the fixation of breast tissue showing the secondary and tertiary planes of manipulation and fixation affected.
Figure 3B:
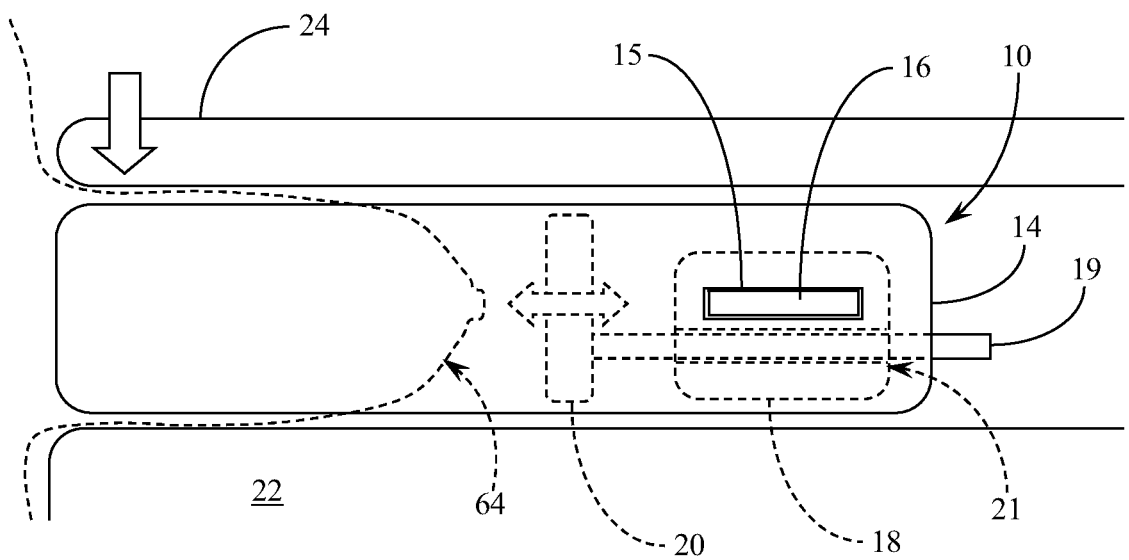
FIG. 3B is an elevational side view of the device of the present invention in use in connection with the fixation of breast tissue showing the primary and tertiary planes of manipulation and fixation affected.

Reference is next made to FIGS. 3A & 3B for a more detailed description of the preferred structure of the caliper device of the present invention. FIGS. 3A & 3B show an embodiment of the invention that includes both the tertiary plane fixation sub-assembly and mechanisms for alternately fixing and releasing the sliding components of the device. These features and functionality are not essential elements of the invention. Fixation of the region of body tissue in only the primary and secondary planes (i.e. not in the tertiary planes) provides significant benefits beyond the existing primary plane fixation systems. In addition, frictional contact between the sliding caliper arms and the bar (and between the center plate bar and center plate positioner) can be sufficient to maintain the positioning of the components around the region of body tissue while in use. Nonetheless, these "optional" elements of the invention provide significant additional benefits and are therefore included in this preferred embodiment. Elimination of these elements requires no significant alteration of the basic structures of the remaining components of the invention.

FIG. 3A is a top plan view of the device of the present invention in use in connection with the fixation of breast tissue (as an example) showing the secondary and tertiary planes of manipulation and fixation affected. The primary plane of fixation is shown in FIG. 3B. Tissue fixation caliper 10 is again shown as comprising first caliper arm (secondary plane fixation) 12 and second caliper arm (secondary plane fixation) 14 which engage with and slide along caliper bar 16. Caliper bar 16 extends through ratcheting aperture 13 in first caliper arm 12 and through ratcheting aperture 15 in second caliper arm 14. The ratcheting mechanisms are structured to allow free sliding movement of arms 12 & 14 inward towards contact with opposing sides of the region of tissue 64 and to resist outward movement on the bar unless sliding ratchet release mechanism 52 (for caliper arm 12) or sliding ratchet release mechanism 54 (for caliper arm 14) are activated. In the example shown in FIG. 3A, the representative region of tissue 64 (a breast) is positioned against image detection plate 22 of typical mammography equipment, providing one side of the parallel planar members that serve to establish fixation in the primary plane. As indicated above, this plate 22 might typically be positioned in a horizontal manner although any angle from horizontal to vertical is possible. The patient is placed adjacent the mammography instrumentation such that the breast under examination (or undergoing intervention) extends from the patient over the plate 22. As seen best in FIG. 3B, the patient forms one of the opposing boundaries of the region of tissue in the tertiary plane in association with center plate fixator 20. Fixation in the secondary plane is, of course, established by caliper arms 12 & 14 as they move inward to contact and thicken the region of tissue 64. For clarity in FIGS. 3A & 3B, the process of fixing the region of tissue 64 in each of the primary, secondary, and tertiary planes has not been completed for any plane, as the device of the present invention is shown in the process of being positioned and adjusted.

The ratcheting mechanisms in the embodiment shown in FIG. 3A include interaction between spring-loaded ratchet pins 53 & 55 positioned within ratcheting apertures 13 & 15 respectively, and ratcheting teeth 60 on the outside edge of caliper bar 16. The angled structures of both spring-loaded ratchet pins 53 & 55 and ratcheting teeth 60 are such as to allow movement of caliper arms 12 & 14 inward but to resist movement outward. The structure of the toothed edge of caliper bar 16 is therefore divided into two regions with the ratchet teeth angled in one direction on the left of center side of the toothed edge and angled in the opposite direction on the right of center side of the toothed edge. Release of the caliper arms to allow sliding in the opposite (non-preferenced) direction involves pushing on the externally accessible circular member of the respective release mechanism 52 & 54. Pushing on the circular member (as an example of a button or other activation mechanism) moves the respective ratchet pin 53 or 55 out of contact with ratcheting teeth 60 to allow movement of the respective caliper arm 12 or 14 in either direction.

As shown in FIG. 3A, tissue fixation caliper 10 includes a tertiary plane fixation mechanism comprising center plate fixator 20. Center plate positioner 18 and center plate bar 19 position center plate fixator 20 on caliper bar 16 in either a fixed central position or in a side to side adjustable manner as described in more detail below. Once again, center plate positioner 18 engages center plate bar 19 to allow free movement of center plate fixator 20 away from center plate positioner 18 and to resist the opposing motion.

Center plate bar 19 extends through ratcheting aperture 17 in center plate positioner 18. This ratcheting mechanism is structured to allow free sliding movement of center plate bar 19 with the attached center plate fixator 20 inward towards the region of tissue (breast) 64, but to resist the reverse movement unless sliding ratchet release mechanism 58 is activated. This ratcheting mechanism in the embodiment shown in FIG. 3A includes interaction between spring-loaded ratchet pin 59 positioned within ratcheting aperture 17, and ratcheting teeth 62 on the outside edge of center plate bar 19. Once again, the angled structures of both spring-loaded ratchet pin 59 and ratcheting teeth 62 are such as to allow movement of center plate bar 19 forward but to resist the reverse motion. Activation of release mechanism 58 allows center plate fixator 20 to slidingly return towards center plate positioner 18.

The optional ratcheting mechanism that allows center plate positioner 18 to move side to side on caliper bar 16 operates in a manner similar to the ratcheting mechanisms for the caliper arms 12 & 14. In this case however, because of the bidirectional angled structure of ratcheting teethe 60, as described above, spring-loaded ratchet pin 57 engages ratcheting teeth 60 on caliper bar 16 in a manner that requires activation of release mechanism 56 for movement away from center but may freely return to center without activation of the release mechanism 56. Once again, there are no significant forces tending to move center plate positioner side to side during use of the caliper device. It is clear from the above description and from FIGS. 3A & 3B that ratcheting apertures 17 & 21 must be offset from each other through center plate positioner 18.

FIG. 3B is an elevational side view of the device of the present invention in use in connection with the process of fixing a region of tissue (a breast) showing the primary and tertiary planes of manipulation and fixation affected. Once again, fixation in each of the planes is shown as incomplete in FIG. 3B in order to more clearly show the various functional elements of the present invention. In FIG. 3B, the region of tissue 64 extends from the patient and is positioned against image detection plate 22 on the primary plane fixation instrumentation. The opposing planar member for the primary plane fixation, compression plate 24, is shown moved into position towards plate 22 to establish the outer boundaries of the region of tissue in the primary plane although, in practice, tissue fixation caliper 10 would be fully positioned and adjusted before plate 24 is "closed" over plate 22.

In the view of FIG. 3B, caliper arm 14 is seen from the side with caliper bar 16 extending out from ratcheting aperture 15. Center plate fixator 20 is likewise seen from the side (in broken line format) positioned between the caliper arms. Center plate bar 19 extends from center plate fixator 20 through ratcheting aperture 21 in center plate positioner 18, out from the back of center plate positioner 18 where it may be manipulated to move center plate fixator 20 towards the region of tissue 64. The manner of positioning and adjusting tissue fixation caliper 10 is described in more detail below.

Figure 4:
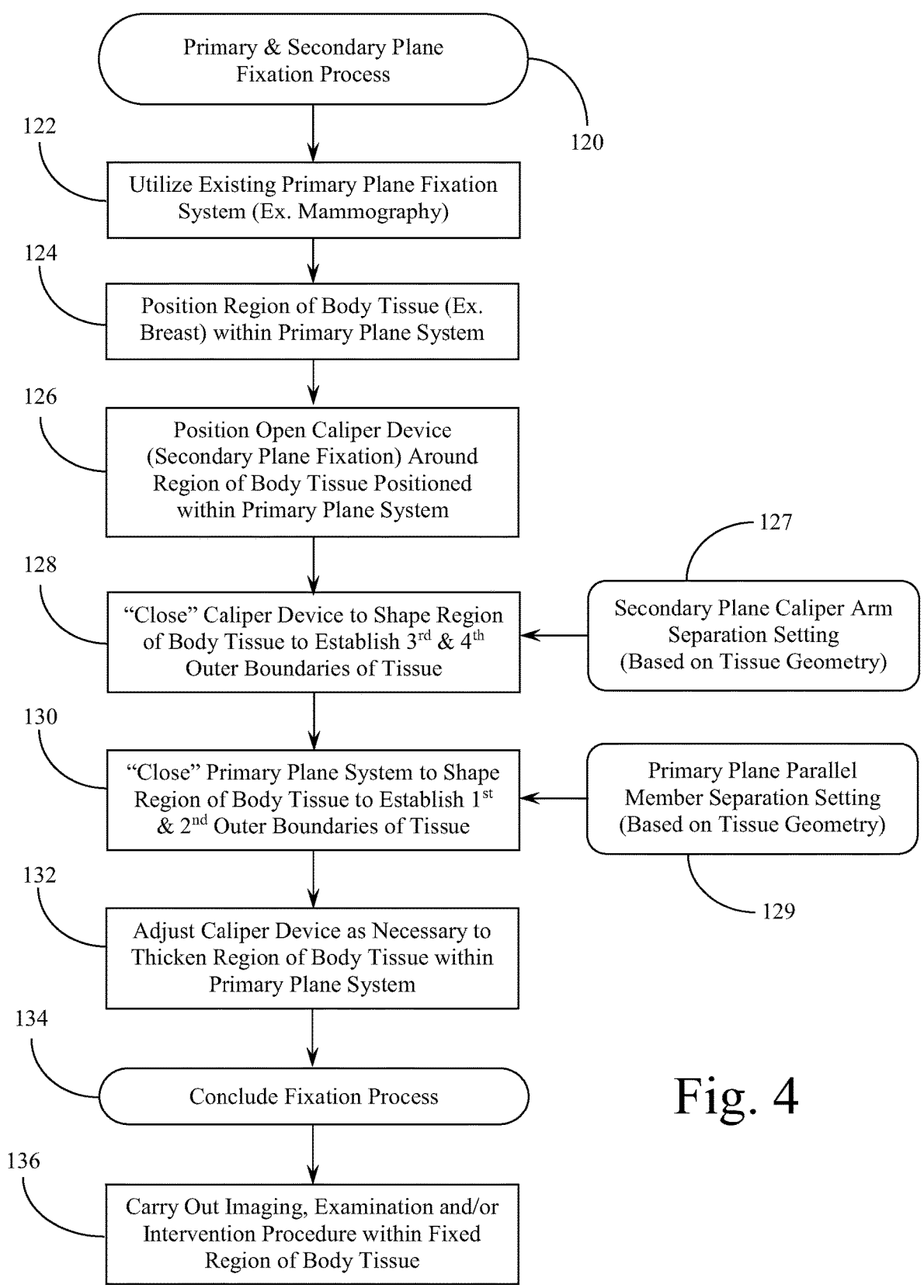
FIG. 4 is a flow chart providing the broad steps associated with the process and method of the present invention to fix a region of tissue in primary and secondary planes.
Figure 5:
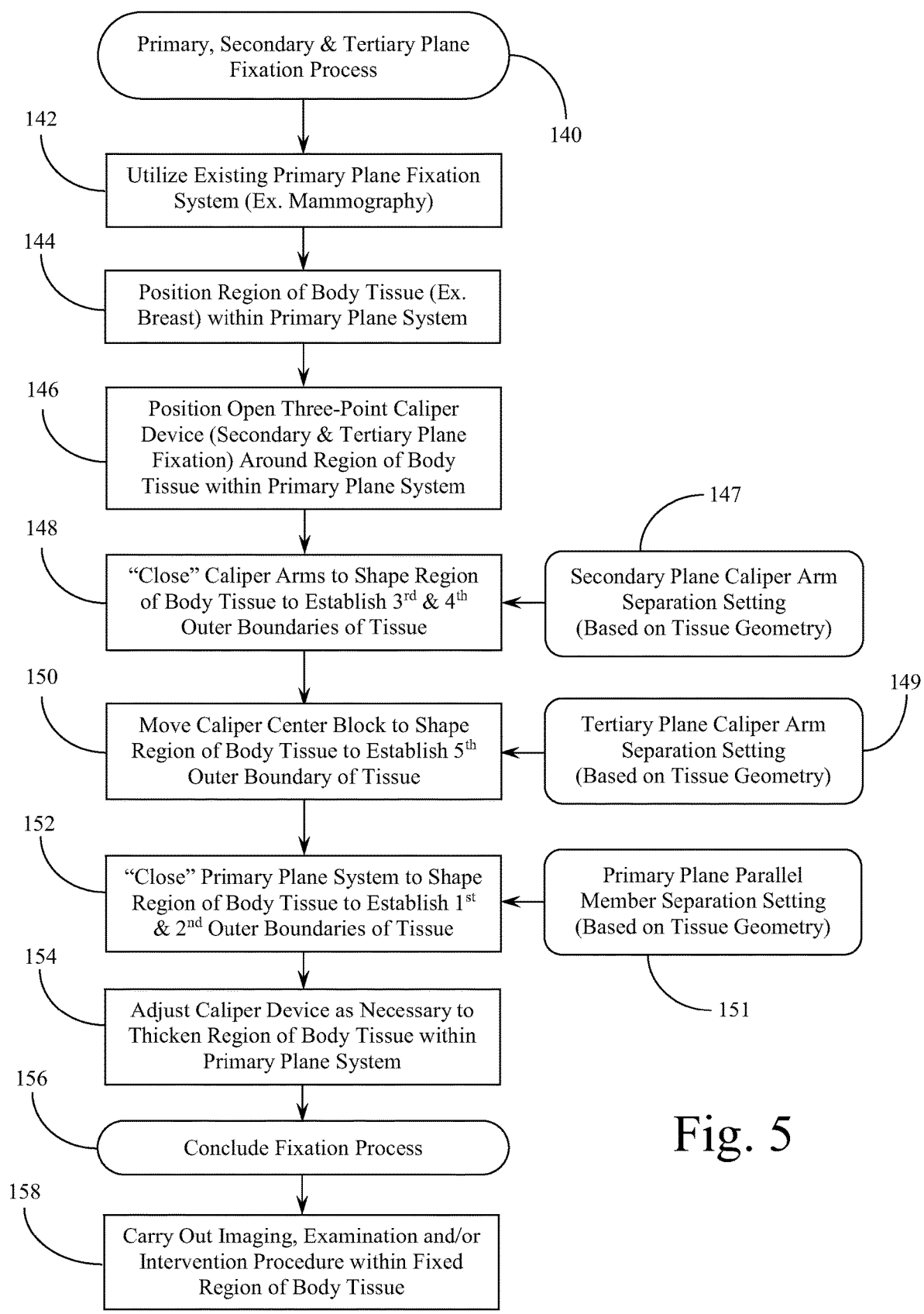
FIG. 5 is a flow chart providing the broad steps associated with the process and method of the present invention to fix a region of tissue in primary, secondary, and tertiary planes.

Reference is next made to FIGS. 4 & 5 which describe in broad terms the use of the device of the present invention to facilitate the imaging of, examination of, diagnosis of, and/or intervention into a region of tissue extending from the body of a patient. FIG. 4 is a flow chart providing the broad steps associated with the process and method of the present invention to fix a region of tissue in primary and secondary planes. FIG. 5 is a flow chart providing the broad steps associated with the process and method of the present invention to fix a region of tissue in primary, secondary, and tertiary planes. FIG. 4 shows at Step 120 the initiation of the process of primary and secondary plane fixation. Step 122 involves initially utilizing existing primary plane fixation instrumentation (a mammography system, for example) in the manner required for such a system. At Step 124, the region of body tissue (a breast of the patient, for example) is positioned within the primary plane fixation system, typically against one of the two parallel planar members. The caliper device of the present invention is "opened" (caliper arms apart) and positioned around (caliper arms on either side) the region of tissue at Step 126.

At this point in the process, the radiologist or medical technician evaluates the volume of the region of tissue and decides on the degree to which the caliper arms should "close" to thicken the region of tissue within the secondary plane. Step 127 involves making this determination and then using the setting at Step 128 to move the caliper arms together to shape the region of tissue and establish the third and fourth outer boundaries of the space. In conjunction with determining a secondary plane setting at Step 127, the radiologist or medical technician evaluates and determines at Step 129 the degree to which the parallel planar members of the primary plane fixation system should be closed. This determination contributes to Step 130 and the process of closing the primary plane system to shape the region of body tissue and establish the first and second outer boundaries of the space. To the extent that the caliper arms of the device remain accessible to the technician, Step 132 provides fine adjustment of the caliper device to further thicken the region of body tissue within the primary plane system. The primary and secondary plane fixation process concludes at Step 134 which is followed by Step 136 involving carrying out the imaging, examination, and/or intervention procedures within the fixed region of body tissue. Although the positioning and adjustment of the device of the present invention is carried out with direct observation of the affect on the spatial dimensions of the region of tissue, and includes the technician's immediate judgement regarding the appropriateness of the settings in both the primary and secondary planes, the caliper bar of the device of the present invention may preferably include a scale that permits notation of the final adjustment and therefore more accurate repeatability where a sequence of examinations or interventions might occur.

Reference is finally made to FIG. 5 which provides a flow chart of the broad steps associated with the process and method of the present invention to fix a region of tissue in primary, secondary, and tertiary planes. FIG. 5 shows at Step 140 the initiation of the process of primary, secondary, and tertiary plane fixation. Step 142 involves initially utilizing existing primary plane fixation instrumentation (a mammography system, for example) in the manner required for such a system. At Step 144, the region of body tissue (a breast of the patient, for example) is positioned within the primary plane fixation system. The three-point caliper device of the present invention is "opened" (caliper arms apart and center plate fixator retracted) and positioned around (caliper arms on either side) the region of tissue at Step 146.

As with the primary/secondary fixation process shown in FIG. 4, at this point in the primary/secondary/tertiary process, the radiologist or medical technician evaluates the volume of the region of tissue and decides on the degree to which the caliper arms should "close" to thicken the region of tissue within the secondary plane. Step 147 involves making this determination and then using the setting at Step 148 to move the caliper arms together to shape the region of tissue and establish the third and fourth outer boundaries of the space. In conjunction with determining a secondary plane setting at Step 147, the physician, radiologist, or medical technician evaluates and determines at Step 149 the extent to which the center plate fixator of the tertiary plane fixation elements of the device should be directed forward towards the region of tissue. This determination contributes to Step 150 and the process of "closing" the tertiary plane system by moving the caliper center plate to shape the region of body tissue and establish the fifth outer boundary of the space. As mentioned above, the sixth outer boundary of the space is essentially established by the body of the patient from which the region of tissue extends.

In conjunction with determining the secondary plane setting at Step 147 and the tertiary plane setting at Step 149, the physician, radiologist, or medical technician evaluates and determines at Step 151 the degree to which the parallel planar members of the primary plane fixation system should be closed. This determination contributes to Step 152 and the process of closing the primary plane system to shape the region of body tissue and establish the first and second outer boundaries of the space. To the extent that the caliper arms and the center plate bar of the device remain accessible to the technician, Step 154 provides fine adjustment of the caliper device to further thicken the region of body tissue within the primary plane system. The primary, secondary, and tertiary plane fixation process concludes at Step 156 which is followed by Step 158 involving carrying out the imaging, examination, and/or intervention procedures within the fixed region of body tissue. Once again, although the positioning and adjustment of the device of the present invention is carried out with direct observation of the effect on the spatial dimensions of the region of tissue, and includes the technician's immediate judgement regarding the appropriateness of the settings in each of the primary, secondary, and tertiary planes, the caliper bar and the center plate bar of the device of the present invention may each preferably include a scale that permits notation of the final adjustment and therefore more accurate repeatability where a sequence of examinations or interventions might occur.

Although the present invention has been described in terms of the foregoing preferred embodiments, this description has been provided by way of explanation only and is not intended to be construed as a limitation of the invention. Those skilled in the art will recognize modifications of the present invention that might accommodate specific medical examination or intervention requirements. Those skilled in the art will further recognize additional methods for modifying the use of the device to accommodate variations in tissue densities and geometries. Such modifications, as to structure, orientation, geometry, and even materials and manufacturing techniques, where such modifications are coincidental to the type of medical application involved, do not necessarily depart from the spirit and scope of the invention.

As indicated above, the size and dimensions of the device of the present invention are generally dictated by the size and geometry of the region of tissue to be examined. In general, the structures of the device of the present invention do not limit the range of dimensions associated with the secondary and tertiary planes. If a tertiary plane fixation is to be used, the minimum "opening" of the caliper arms will be limited by the width of the center plate fixator positioned between the caliper arms. In most cases, a minimum caliper arm opening of 1-2 cm would be adequate for the device's intended uses. The only other limitation established by the structures of the device of the present invention is the minimum "opening" of the parallel planar members of the primary plane fixation system, which minimum is set by the height (thickness) of the two caliper arms. In most cases, a caliper arm height (thickness) of 1-4 cm is adequate for the device's intended uses. In determining the appropriate thickness of the caliper arms (and the caliper as a whole) some consideration should be given to minimizing any edge gap between adjoining planes where over-compression of the region of tissue might "pinch" edge portions of the tissue between device components and the parallel planar members of the primary plane fixation system. This balancing speaks to the preference for having fixation caliper devices in a range of sizes. A disposable kit of components, for example, could contain a single caliper bar with a selection of caliper arms of varying thicknesses. For the optional tertiary fixation device, a single center plate bar could be provided with a range of interchangeable center plate fixators of varying size. In general, however, the low cost of materials and the ease of manufacture make fully operational calipers of small, medium, and large sizes (as examples) a preferred manner of allowing the physician, radiologist, or medical technician to quickly choose the best caliper size for the particular situation.

I claim:

1. An apparatus for fixing the outer boundaries of a region of human breast tissue in a secondary plane during medical imaging and/or intervention; the region of human breast tissue extending from an individual and fixed in a primary plane by a separate device having parallel planar members configured to be moved, the apparatus comprising:
   a caliper bar having first and second end portions and a center portion; and
   first and second caliper arms slidingly positioned on the caliper bar, each of the caliper arms comprising a mechanism for fixing the caliper arm in a stable position on the caliper bar;
   wherein the apparatus is positioned on at least two sides of the region of human breast tissue between the movable parallel planar members.

2. The apparatus of claim 1 wherein the mechanisms for fixing the caliper arms on the caliper bar each comprise a ratcheting assembly interactive between the caliper bar and each of the caliper arms.

3. The apparatus of claim 1 wherein the mechanism for fixing the caliper arms on the caliper bar each comprise a friction grip assembly interactive between the caliper bar and each of the caliper arms.

4. The apparatus of claim 2 wherein each ratcheting assembly comprises: a toothed edge of the caliper bar; a spring-loaded pin positioned and preferenced to engage the toothed edge of the caliper bar; and a push member operably connected to the spring-loaded pin, the push member configured to be moved and to correspondingly move the spring-loaded pin to remove it from engagement with the toothed edge.

5. The apparatus of claim 4 wherein the toothed edge of the caliper bar comprises a first region interactive with the ratcheting assembly on the first caliper arm and a second region interactive with the ratcheting assembly on the second caliper arm, the first region comprising angled teeth that allow the first caliper arm to freely slide outward from the center portion of the caliper bar but resist inward motion, the second region comprising oppositely angled teeth that allow the second caliper arm to freely slide outward from the center portion of the caliper bar but resist inward motion.

6. The apparatus of claim 1 wherein the first and second caliper arms comprise generally rectangular solid shaped elements each having a proximal end extending towards the individual, and a distal end extending away from the individual, each caliper arm defining an aperture through its distal end for sliding engagement of the caliper bar.

7. The apparatus of claim 6 wherein the caliper arms have a thickness dimension in the range of 1-4 cm, the thickness of the caliper arms representing a minimum separation distance between the parallel planar members fixing the region of tissue in the primary plane.

8. An apparatus for fixing the outer boundaries of a region of human breast tissue in a secondary plane and a tertiary plane during medical imaging and/or intervention; the region of human breast tissue extending from an individual and fixed in a primary plane by a separate device having parallel planar members configured to be moved, the apparatus comprising:
- a caliper bar having first and second end portions and a center portion;
- first and second caliper arms slidingly positioned on the caliper bar, each of the caliper arms comprising a mechanism for fixing the caliper arm in a stable position on the caliper bar; and
- a center plate fixator assembly slidingly positioned on the caliper bar between the first and second caliper arms, the center plate fixator assembly comprising a mechanism for fixing the assembly in a stable position on the caliper bar;
- wherein the apparatus is positioned on at least three sides of the region of human breast tissue between the movable parallel planar members.

9. The apparatus of claim 8 wherein the center plate fixator assembly further comprises:
- a base member slidingly positioned on the caliper bar;
- a center plate fixator bar slidingly engaged by the base member, the center plate fixator bar having proximal and distal end portions and oriented orthogonal to the caliper bar; and
- a center plate fixator face oriented in a plane orthogonal to the first and second caliper arms and positioned on the center plate fixator bar at the proximal end thereof.

10. The apparatus of claim 8 wherein the mechanisms for fixing the caliper arms on the caliper bar each comprise a ratcheting assembly interactive between the caliper bar and each of the caliper arms.

11. The apparatus of claim 10 wherein each ratcheting assembly comprises: a toothed edge of the caliper bar; a spring-loaded pin positioned and preferenced to engage the toothed edge of the caliper bar; and a push member operably connected to the spring-loaded pin, the push member configured to be moved and to correspondingly move the spring-loaded pin to remove it from engagement with the toothed edge.

12. The apparatus of claim 11 wherein the toothed edge of the caliper bar comprises a first region interactive with the ratcheting assembly on the first caliper arm and a second region interactive with the ratcheting assembly on the second caliper arm, the first region comprising angled teeth that allow the first caliper arm to freely slide outward from the center portion of the caliper bar but resist inward motion, the second region comprising oppositely angled teeth that allow the second caliper arm to freely slide outward from the center portion of the caliper bar but resist inward motion.

13. The apparatus of claim 8 wherein the first and second caliper arms comprise generally rectangular solid shaped elements each having a proximal end extending towards the individual, and a distal end extending away from the individual, each caliper arm defining an aperture through its distal end for sliding engagement of the caliper bar.

14. The apparatus of claim 13 wherein the caliper arms have a thickness dimension in the range of 1-4 cm, the thickness of the caliper arms representing a minimum separation distance between the parallel planar members fixing the region of tissue in the primary plane.

15. The apparatus of claim 9 wherein the base member further comprises a mechanism for fixing the center plate fixator bar in a stable position through the base member.

16. The apparatus of claim 15 wherein the mechanism for fixing the center plate fixator bar in a stable position through the base member comprises a ratcheting assembly interactive between the center plate fixator bar and the base member.

17. The apparatus of claim 16 wherein the ratcheting assembly comprises: a toothed edge of the center plate fixator bar; a spring-loaded pin positioned to and preferenced to engage the toothed edge of the center plate fixator bar; and a push member operably connected to the spring-loaded pin, the push member configured to be moved and to correspondingly move the spring-loaded pin to remove it from engagement with the toothed edge.

18. The apparatus of claim 15 wherein the mechanism for fixing the center plate fixator bar in a stable position through the base member comprises a friction grip assembly interactive between the center plate fixator bar and the base member.

19. A method for fixing a region of body tissue during medical imaging, examination, and/or intervention by setting the outer boundaries of the region of body tissue, the method comprising the steps of:
- providing a primary plane fixation system comprising a pair of parallel planar members, the primary plane fixation system initially in an open condition with the parallel planar members spaced apart at a primary plane first separation distance;
- positioning the region of body tissue within the primary plane fixation system between the parallel planar members;
- providing a secondary plane fixation device comprising a caliper bar with first and second caliper arms slidingly positioned on the caliper bar, each of the caliper arms comprising a mechanism for fixing the caliper arm in a stable position on the caliper bar, the secondary plane fixation device initially in an open condition with the first and second caliper arms spaced apart at a secondary plane first separation distance;
- positioning the secondary plane fixation device around the region of body tissue within the primary plane fixation system, the first and second caliper arms bracketing the region of body tissue between the parallel planar members;
- moving the first and second caliper arms towards each other to establish a secondary plane, second separation distance between the caliper arms, whereby at the secondary plane, second separation distance, the caliper arms contact and shape the region of body tissue to establish third and fourth outer boundaries of the region of tissue in the secondary plane; and
- moving the parallel planar members towards each other to establish a primary plane second separation distance between the members, whereby at the primary plane second separation distance, the parallel planar members contact and shape the region of body tissue to establish first and second outer boundaries of the region of tissue in the primary plane.

20. The method of claim 19 further comprising the steps of:
- providing a tertiary plane fixation device comprising a center plate fixator assembly positioned on the caliper bar of the secondary plane fixation device between the first and second caliper arms, the center plate fixation assembly comprising a movable center plate fixator face oriented in a plane orthogonal to the first and second caliper arms, the tertiary plane fixation device initially in a retracted condition with the center plate fixator face spaced apart distally from the region of body tissue; and moving the center plate fixator face proximally towards the region of body tissue to establish a tertiary plane separation distance, whereby at the tertiary plane separation distance the center plate fixator face contacts and shapes the region of body tissue to establish a fifth outer boundary of the region of body tissue in the tertiary plane, a sixth dimensional boundary of the region of body tissue being established by the body of the individual from which the region of body tissue extends.

* * * * *